United States Patent
Levy et al.

(10) Patent No.: US 9,855,282 B2
(45) Date of Patent: *Jan. 2, 2018

(54) METHOD FOR SCHEDULING OVULATION

(71) Applicant: LABORATOIRE HRA-PHARMA, Paris (FR)

(72) Inventors: Delphine Levy, Bagnolet (FR); Erin Gainer, Paris (FR)

(73) Assignee: Laboratoire HRA-Pharma, Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 15/352,319

(22) Filed: Nov. 15, 2016

(65) Prior Publication Data

US 2017/0056417 A1    Mar. 2, 2017

Related U.S. Application Data

(63) Continuation of application No. 14/774,857, filed as application No. PCT/EP2014/055022 on Mar. 13, 2014, now Pat. No. 9,522,154.

(60) Provisional application No. 61/781,737, filed on Mar. 14, 2013.

(30) Foreign Application Priority Data

Mar. 14, 2013  (EP) .................................. 13305287

(51) Int. Cl.
*A61K 31/57* (2006.01)
*A61B 17/435* (2006.01)
*A61K 9/00* (2006.01)

(52) U.S. Cl.
CPC ............ *A61K 31/57* (2013.01); *A61B 17/435* (2013.01); *A61K 9/0053* (2013.01)

(58) Field of Classification Search
CPC ....................................................... A61K 31/57
See application file for complete search history.

(56) References Cited

U.S. PATENT DOCUMENTS 9,522,154 B2 * 12/2016 Levy ...................... A61K 31/57

* cited by examiner

*Primary Examiner* — Rei Tsang Shiao
(74) *Attorney, Agent, or Firm* — Leason Ellis LLP

(57) ABSTRACT

The invention relates to a method for scheduling ovulation in a female subject, which method comprises administering ulipristal acetate (UPA) to the female subject during the follicular phase.

14 Claims, 1 Drawing Sheet

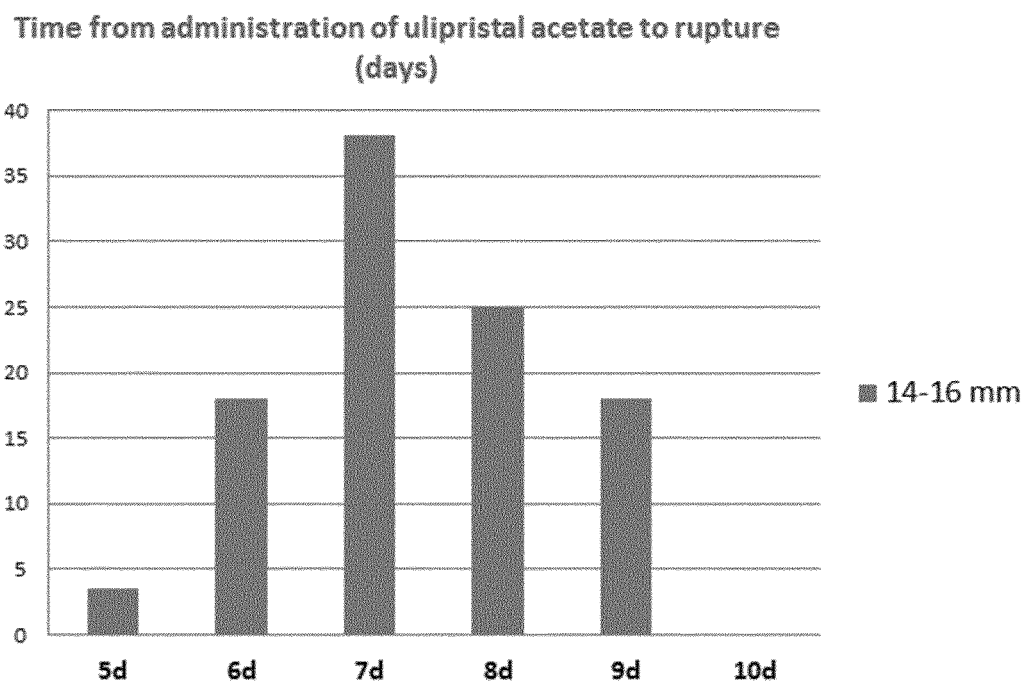

METHOD FOR SCHEDULING OVULATION

The present invention relates to a method for scheduling ovulation and improving fertility in a female subject.

BACKGROUND OF THE INVENTION

The ovarian/menstrual cycle is a complex process characterized by an estrogen rich follicular phase and, after ovulation, a progesterone rich luteal phase. Luteal phase has a duration of approximately 14 days resulting while the duration of the follicular phase may vary considerably resulting in an intermenstrual interval of 20 to more than 45 days. Habitual cycle length in the majority of women however varies from 25 to 34 days.

The onset of menstruation is generally considered to be the beginning of a new menstrual cycle and is generally counted as Day 1.

After each menses, the ovaries are stimulated by follicle stimulating hormone (FSH) released by the pituitary to grow a cohort of growing follicles. These follicles each comprise an oocyte (egg cell) which is enveloped by an orb of granulosa cells. During growth of the follicles several layers of granulosa cells are being formed. Follicle maturation during the normal menstrual cycle occurs in 12-14 days. Gradually, one follicle becomes dominant and the others become atretic. Maturation of the dominant follicle usually takes 5-7 days. As the number of granulosa cells increases more estrogen is secreted by these cells.

Once the dominant follicle has reached maturity, the follicle will burst (ovulate) under the action of a surge of luteinising hormone (LH) which is released by the pituitary in response to the increased blood serum estrogen level (positive feedback). The oocyte is discharged from the follicle into the ampulla of the Fallopian tube, where fertilization may take place. The oocyte or embryo is transported to the uterus in 5-7 days, where implantation may occur in the midluteal phase.

The follicle that has discharged the oocyte is transformed into a new hormone producing organ, the corpus luteum. The corpus luteum produces amongst others progesterone and estrogens. The corpus luteum has a limited lifespan of about 12-14 days, unless pregnancy occurs. During the second part of that period, it ceases functioning, and as a result the blood level of estrogens and progesterone drops. The decline of progesterone causes shedding of the lining of the uterus and thus menstruation.

In particular in the area of ovulation induction, the past decades have shown the development and commercial introduction of numerous drugs assisting in fertility management of infertile couples. Amongst others, these include anti-estrogens (like clomiphene citrate and tamoxifen citrate), pulsatile gonadotropin releasing hormone (GnRH), purified and recombinant gonadotropins, and GnRH agonists and antagonists. The specific drugs used and administration regimens chosen largely depend on the goal of the treatment, e.g. the induction of mono-ovulation in anovulatory females or the controlled ovarian hyperstimulation to induce multiple follicular development as an element in assisted reproductive technologies (ART).

Even when the couple does not suffer from any disorder which may affect their fertility, the woman may confront difficulties to get pregnant. The fertile window is very short and generally lasts five days, typically from four days before ovulation to the day of ovulation (included). The ovulation date varies from menstrual cycle to menstrual cycle for the same woman, as the length of the menstrual cycle also varies. It may thus be very difficult for a woman to predict the occurrence of the ovulation and thus to schedule fertilizing intercourses. Thus, there is still a need for a safe drug that would not only induce but, most importantly, also control the timing of ovulation.

Indeed scheduling the event of ovulation, for example in females who suffer from ovulation dysregulation, irregular menstrual cycle, would be very helpful for improving infertility management.

SUMMARY OF THE INVENTION

The inventors now more particularly propose to administer a female with ulipristal acetate (UPA), during the follicular phase of menstrual cycle. Preferably, ulipristal acetate is administered between the $3^{rd}$ day and the 12th day of menstrual cycle in a woman, so as to induce ovulation about 4 to 9 days after administration of UPA.

This facilitates fertilization i.e. the achievement of pregnancy. More particularly, this helps the woman who wishes to become pregnant schedule an intercourse at a moment when she has ovulated or is about to ovulate, i.e. 4 to 9 days, such as 4 to 7 days or 6 to 8 days, after administration of UPA.

Alternatively, an artificial insemination can be scheduled during that particular period of time, i.e. 4 to 9 days, such as 4 to 7 days or 6 to 8 days, after administration of UPA.

At last, if desired, collection of an oocyte can be scheduled during that particular period of time, i.e. 4 to 9 days, such as 4 to 7 days or 6 to 8 days, after administration of UPA.

It is thus provided a method for scheduling ovulation in a female subject, in a non-human mammal or in a woman who wants to get pregnant, which method comprises administering ulipristal acetate (UPA) or a metabolite thereof to the female subject during the follicular phase of the menstrual cycle.

It is more particularly provided a method for improving fertility in a woman, which method comprises administering ulipristal acetate (UPA) to the woman between the $3^{rd}$ day and the 12th day of her menstrual cycle, preferably between the 4th day and the 8th day of her menstrual cycle.

It is also provided a method for scheduling a sexual intercourse at a day when a woman is likely to be fertile, which method comprises administering ulipristal acetate (UPA) or a metabolite thereof to the woman between the $3^{rd}$ day and the $12^{th}$ day of her menstrual cycle.

A further object is a method for fertilizing a woman who wants to become pregnant, which method comprises:
(i) administering ulipristal acetate (UPA) or a metabolite thereof to the woman between the $3^{rd}$ day and the 12th day of her menstrual cycle, and
(ii) scheduling an intercourse or an insemination for said woman about 4 to 9, preferably 5, 6, 7 or 8 days after the administration of ulipristal acetate or a metabolite thereof.

It is also described a method for fertilizing a woman in need thereof comprising the steps of:
i. Administering said subject with an effective amount of ulipristal acetate, or a metabolite thereof, between the $3^{rd}$ day and the $12^{th}$ day of her menstrual cycle, and
ii. Inseminating said subject about 4 to 9 days, for instance 4 to 7 days or 6 to 8 days, after administering ulipristal acetate or a metabolite thereof.

In a further embodiment, a method for obtaining the production of a fertilizable oocyte before fertilization by an artificially reproductive technique is contemplated, which method comprises administering ulipristal acetate (UPA) or a metabolite thereof to a female subject during the follicular phase, e.g. between the 3rd day and the 12th day of her menstrual cycle if the subject is a woman, and optionally collecting the fertilizable oocyte about 4 to 9 days e.g. 4 to 7 days, preferably 5 to 6 days or 6 to 8 days, after administration.

At last it is provided a method for fertilizing a female subject, preferably a non-human mammal, in need thereof, comprising the steps of:

i. Administering said subject with an effective amount of ulipristal acetate, or a metabolite thereof, during the follicular phase of the menstrual cycle, and ii. Inseminating said subject about 4 to 9 days e.g. 4 to 7 days, preferably 5 to 6 days or 6 to 8 days, after administering ulipristal acetate or a metabolite thereof.

DETAILED DESCRIPTION OF THE INVENTION

Ulipristal Acetate and SPRMs

Ulipristal acetate is a selective progesterone receptor modulator (SPRM) (Stratton et al, Human Reproduction, 2000, 15(5): 1092-1099). In the context of the invention, a SPRM is a compound that is a progesterone analog and that has a mixed agonist/antagonist profile of action, which is tissue specific. A SPRM may act as an agonist in some tissues while as an antagonist in others.

Ulipristal acetate, formerly known as CDB-2914, designates within the context of this application 17α-acetoxy-11β-[4-N,N-dimethylamino-phenyl]-19-norpregna-4,9-diene-3,20-dione, represented by formula I:

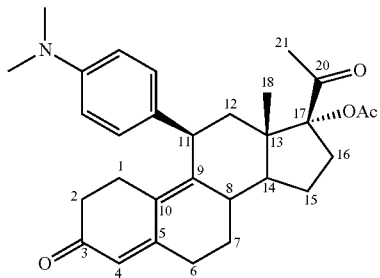

I

Ulipristal acetate, and methods for its preparation, are described e.g., in U.S. Pat. Nos. 4,954,490; 5,073,548; and 5,929,262, as well as in international patent applications WO2004/065405 and WO2004/078709.

Metabolites of ulipristal acetate, include those described in Attardi et al, Journal of Steroid Biochemistry & Molecular Biology, 2004, 88: 277-288, e.g. monodemethylated CDB-2914 (CDB-3877); didemethylated CDB-2914 (CDB-3963); 17alpha-hydroxy CDB-2914 (CDB-3236); aromatic A-ring derivative of CDB-2914 (CDB-4183).

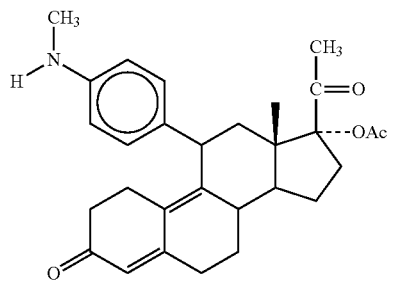

monodemethylated CDB-2914

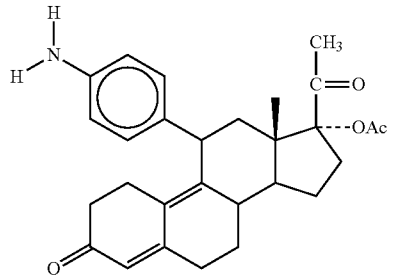

didemethylated CDB-2914

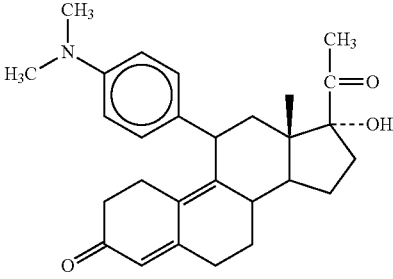

17α-hydroxy CDB-2914

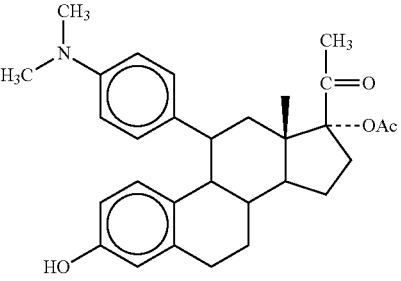

aromatic A-ring CDB-2914

Ulipristal acetate is commercialized under the trade name EllaOne® for emergency contraception. It has been shown that a single dose of 30 mg of ulipristal acetate is safe and effective to avoid an unwanted pregnancy when it is administered within 72 hours or 120 hours after the intercourse (Creinin et al., Obstetrics and Gynecology, 2006, 108(5): 1089-1097; Glasier et al, Lancet. 2010, 375(9714):555-62; Fine et al, Obstet Gynecol. 2010, 115:257-63). As a SPRM, ulipristal acetate has partial agonistic as well as antagonistic effects on the progesterone receptor.

Other SPRMs may be useful in the present invention, in lieu of ulipristal acetate. Examples of non-steroidal SPRM are cited in: Dong et al., Steroids, 2004, 69:201-207, Zhi et al., J Med Chem, 2003, 46:4104-4112 and Zhi et al., Curr Top Med Chem, 2008, 8:766-780.

Preferably, steroidal derivative SPRM are chosen among steroidal derivatives with a substituted aryl group in position 11β. Preferred aryl groups comprise the 4-(dimethylamino) phenyl, the 4-acetylphenyl and the benzaldoxime. Examples of such steroidal SPRM may be found in the following publications: Rao et al., Steroids, 1998, 63:523-530 and Chabbert-Buffet et al., Human Reproduction Update, 2005, 11, 293-307. More particularly, Chabbert-Buffet et al. discloses mifepristone, onapristone, asoprisnil, ulipristal acetate (UPA) or active metabolites thereof, Org 33628 and Org 31710 as SPRM.

The Subject

The subject may be any female mammal of child-bearing age or any pre-menopausal female, for instance peri-menopausal female.

In a preferred embodiment, the subject is human, i.e. a woman. More precisely, the subject is a woman of child-bearing age who wants to become pregnant.

In some embodiments, the woman is a healthy subject. In the context of the invention, a "healthy subject" refers to a woman who does not suffer from any disorder or disease which may impair her fertility. In particular, the woman is able to ovulate, which means that she does not need any administration of an ovulation inducer such as clomiphene citrate, hCG or FSH in order to ovulate.

However, said woman may experiment variable menstrual cycles.

In some embodiments, the woman may experiment variations on the day of ovulation. As used herein "a variable day of ovulation" means that the ovulation does not regularly occur on the same day of the menstrual cycle, said day of ovulation changes from one cycle to another, and thus, the duration of the follicular phase may vary from menstrual cycle to menstrual cycle. Typically, the woman may experience length variations of her follicular phase up to 10 days, preferably up to 8 days, such as 1, 2, 3, 4 or 5 days. The woman may alternatively (or additionally) display menstrual cycles with variable length, which means that the length of her menstrual cycles may vary from cycle to cycle. Indeed, the woman may experience cycle length variations up to 10, preferably up to 8 days between the shortest and longest cycle within one year. Preferably, the variation in cycle length is of few days, for example from 1 to 8 days, and preferably of 1, 2, 3, 4, or 5 days. For instance, the woman may display menstrual cycles, which length varies from 26 to 30 days.

Alternatively, said woman may have regular menstrual cycles with regular ovulation, but with a length of more than 28 days, for example up to about 40 days, preferably up to 35 days.

In some embodiments, the subject is a woman who experiments a variation of less than 8 days in menstrual cycle length and/or menstrual cycles with length of less than 40 days, typically from 21 to 35 days.

In some preferred embodiments, the method of the invention is dedicated to a woman displaying at least one (i.e. 1, 2 or 3) of the following features:
 a variable day of ovulation,
 menstrual cycles with variable lengths, and
 menstrual cycles with a mean length up to 40 days, preferably up to 35 days.

In an additional embodiment, the woman does not suffer from any disorder or disease impairing her fertility. Indeed, the woman may experiment some variations in menstrual cycles such as a variable day of ovulation or a variation in menstrual cycle length. However, these variations are physiological and non-pathological variations.

In some other embodiments, the subject is a peri-menopausal woman.

In some further embodiments, the subject is a woman who suffers from irregular menstrual cycles, this means that the variation in the length of menstrual cycles is more than 10 days, for instance more than 15 days. In some additional embodiments, the woman suffers from ovulation dysregulation, for example infrequent ovulations such as oligomenorrhea. In such a case, the woman may suffer from a disorder or a disease impairing her fertility. In other words, the condition experimented by the women refers to a pathological condition.

In another embodiment, the subject is a non-human mammal, including companion animals or pets (a cat, a dog), or live stocks (such as cows, horses, pigs . . . ).

The Regimen

Ulipristal acetate or a metabolite thereof is administered during the follicular phase.

Ulipristal acetate or a metabolite thereof may be administered before or during the LH surge e.g. at the beginning of the LH surge. In a preferred embodiment, ulipristal acetate or a metabolite thereof is administered before the LH surge.

Thus, ulipristal acetate or a metabolite thereof is generally administered between the $3^{rd}$ and the $12^{th}$ day. For instance, ulipristal acetate or a metabolite thereof can be administered on day $4^{th}$, $5^{th}$, $6^{th}$, $7^{th}$, $8^{th}$ or $9^{th}$ of the menstrual cycle. Preferably ulipristal acetate or a metabolite thereof is administered between the $4^{th}$ and the $8^{th}$ day, still preferably between the $5^{th}$ and the $7^{th}$ day of the menstrual cycle to a woman.

In some embodiments, ulipristal acetate or a metabolite thereof may be administered up to $20^{th}$ days of the menstrual cycle, in particular when the woman experiments menstrual cycles with a mean length of more than 35 days.

In other embodiments, ulipristal acetate or a metabolite thereof is administered to the woman during the follicular phase, at a stage wherein the diameter of the dominant follicle is at most 18 mm, preferably at most 16 mm, for instance from 14 to 16 mm.

Ulipristal acetate or a metabolite thereof may be preferably administered at a dosage of 5 to 60 mg, preferably 10 to 40 mg, still preferably 20 to 30 mg, even more preferably 30 mg.

Ulipristal acetate or a metabolite thereof may be administered once, twice or every day during the follicular phase of the menstrual cycle, ie between the $3^{rd}$ and the $12^{th}$ day of the menstrual cycle in a woman.

In a preferred embodiment, a single (preferably oral) administration of ulipristal acetate or a metabolite thereof is proposed. The preferred dosage for such a single administration is from 20 mg to 40 mg, e.g. 30 mg of ulipristal acetate or a metabolite thereof Administration Routes and Formulation Ulipristal acetate or a metabolite thereof may be administered by various routes, e.g., orally, by injection, transdermally or vaginally. As mentioned above, a preferred administration route is the oral route. However, the agent may also be administered by injection, or with a patch, in a gel, or a vaginal ring, for instance.

Methods and compositions for making useful dosage units are well-known to those skilled in the art. For example, conventional techniques for making tablets and pills, containing active ingredients, are described in the standard reference, Chase et al., Remington's Pharmaceutical Sciences, (16th ed., Mack Publishing Co., Easton. Pa., U.S.A., 1980) ("Remington's"), at pages 1553 through 1584. Conventional techniques for making powders, and their composition are described at pages 1535 through 1552 of the reference. Conventional techniques for coating pharmaceutical dosage forms are described at pages 1585 to 1593 of Remington's.

Oral solid dosage forms are preferably compressed tablets, that may be coated or uncoated, or capsules.

Capsules are solid dosage forms using preferentially either a hard or soft gelatine shell as a container for the mixture of the active ingredient and inert ingredients. Procedures for production and manufacture of hard gelatin and soft elastic capsules are well known in the art.

Compressed tablets may contain any excipients which are diluents to increase the bulk of the active ingredient so that production of a compressed tablet of practical size is possible. Binders, which are agents which impart cohesive qualities to powdered materials are also necessary. Starch, gelatine, sugars such as lactose or dextrose, and natural and synthetic gums are used. Disintegrants are necessary in the tablets to facilitate break-up of the tablet. Disintegrants include starches, clays, celluloses, algins, gums and cross-linked polymers. Lastly small amounts of materials known as lubricants and glidants are included in the tablets to prevent adhesion to the tablet material to surfaces in the manufacturing process and to improve the flow characteristics of the powder material during manufacture. Colloidal silicon dioxide is most commonly used as a glidant and compounds such as talc or stearic acids are most commonly used as lubricants. Procedures for the production and manufacture of compressed tablets are well known by those skilled in the art.

In a particular embodiment, ulipristal acetate or a metabolite thereof is used in form of an uncoated tablet wherein ulipristal acetate or a metabolitie thereof is mixed with excipients that are lactose monohydrate, povidone (polyvinylpyrrolidone), croscarmellose sodium, and magnesium stearate (e.g. as described in international patent application WO2010/066749).

Scheduling Ovulation and Improving Fertility

Ulipristal acetate or a metabolite thereof, when administered during the follicular phase, e.g. between the $3^{rd}$ and the $12^{th}$ day in a woman, induces ovulation about 4-9 days after. In some preferred embodiments, the ovulation occurs 5 to 9 days after the administration of ulipristal acetate. For instance, the ovulation occurs on day 5, 6, 7, 8 or 9, preferably on day 6, 7 or 8, after the administration of ulipristal acetate. This allows scheduling a natural intercourse, artificial insemination or collection of the oocyte at the most appropriate timing for the subject to be fertile.

In a particular aspect, the invention is useful for any woman who wants to become pregnant. The method of the invention enables the woman to schedule the days of her fertilizing sexual intercourses according to the predicted/predictable day of her ovulation, and thus to maximize her chances of getting pregnant. The method of the invention is expected to reduce the mean time required for a woman to become pregnant.

As mentioned above, in some embodiments, the woman is a healthy woman who may experiment menstrual cycles with variable length, variable day of ovulation and/or with length up to 40 days, preferably up to 35 days.

The method of the invention is thus a method for scheduling ovulation. In another aspect, the method of the invention is a method for fertilizing a woman in need thereof, i.e. for achieving pregnancy in a woman in need thereof.

More generally, the invention relates to the use of ulipristal acetate for scheduling ovulation in a woman.

In another aspect, the invention is useful in females who suffer from ovulation dysregulation or irregular menstrual cycle. Thus, the method of the invention may be a method for improving fertility or for treating infertility in these females.

For instance, it is expected that the method of the invention is able to shorten the follicular phase in women having extended menstrual cycles, i.e. menstrual cycles of at least 36 days or more, so as to increase the frequency of ovulation, whereby the fertility of the women is improved.

In some embodiments, for women who show irregular menstrual cycles or amenorrhea, a progestative agent (such as dydrogesterone), preferably during 10 days, can be administered to trigger menses, before treating with ulipristal acetate or a metabolite thereof.

The method of the invention is useful for scheduling or timing intercourses or insemination to achieve pregnancy.

A natural coït, i.e. an intercourse (or the subject is a non-human mammal, mating) can be scheduled about 4 to 9, preferably 5-8 days, more preferably 6, 7, or 8 days after administering ulipristal acetate or a metabolite thereof. In some embodiments, several natural intercourses can be scheduled. Preferably, natural intercourses occur no more than every two days so as to preserve the quality of the sperm. For instance, natural intercourses can be scheduled on $4^{th}$, $6^{th}$ and $8^{th}$ day; or on $5^{th}$, and $9^{th}$ following the administration of ulipristal acetate so as to promote the achievement of pregnancy. In another example, a first intercourse can be scheduled on day 6 and a second intercourse on day 8 after the administration of ulipristal acetate or a metabolite thereof.

The method of the invention is also useful to schedule ovulation before fertilization by an artificial reproductive technique. The artificial reproductive technique may be artificial insemination such as vaginal sperm injection, intrauterine insemination (IUD, intracervix sperm injection.

The subject can then be inseminated about 4 to 9 days, preferably 5-8, more preferably 6, 7, or 8 days, after administering ulipristal acetate or a metabolite thereof.

Alternatively artificial reproductive technique may be intracytoplasmic sperm injection (ICSI), or in vitro fertilization (IVF). Artificial insemination such as ICSI or IVF may be needed even when the woman has no fertility disorder and in particular no ovulation dysregulation, but when the infertility is due to the male partner, e.g. where sperm counts are very low.

In some embodiment, ulipristal acetate or a metabolite thereof may be administered alone, without any further medicament acting on the ovarian cycle, in particular without any ovulation inducer or without any agent able to delay LH surge such as GnRH antagonists.

In particular, the female subject, in particular the human female subject, is not administered with any substance having follicle stimulating hormone activity, preferably nor any meiosis and luteinisation inducing substance. For instance, the woman does not experiment any controlled ovarian hyperstimulation.

The present invention also relates to the use of ulipristal acetate or a metabolite thereof for the manufacture of a medicament for improving fertility and/or for scheduling ovulation of a woman in need thereof.

In a further aspect, the invention relates to the use of ulipristal acetate or a metabolite thereof for improving fertility and/or for scheduling ovulation of a woman in need thereof.

The present invention further contemplates a method for synchronizing luteal phase in two female subjects, for instance in the prospect of transferring a fertilized oocyte from a donor to a recipient, e.g. a surrogate mother. In such a method, a first female subject from whom the oocyte is collected, and/or a second female into whom the oocyte is implanted, are administered with ulipristal acetate or a metabolite thereof, so that the luteal phases of the two female subjects become synchronized. The hormonal state of the second female who is to receive the implantation of the fertilized oocyte then allows her to carry on with the pregnancy.

In the veterinary or breeding fields, scheduling ovulation may be particularly useful for synchronizing ovulation in a herd (i.e. at least two non-human mammals).

DESCRIPTION OF THE FIGURES

FIG. 1 shows the time from the administration of ulipristal acetate to the rupture of the follicle (see Example 2). The ovulation occurred 5 to 9 days after ovulation. Most of the women ovulate on days 6, 7 or 8 after the administration of ulipristal acetate.

EXAMPLE 1

In an open-label designed trial, 12 women received once weekly (Q7D) treatment with ulipristal acetate (30 mg oral tablet) for eight consecutive weeks starting on 7 days±1 day after the onset of menses in the first cycle; and 11 women received ulipristal acetate 30 mg every 5 days (Q5D) for 8 weeks. Neither regimen inhibited ovulation throughout the duration of treatment in a majority of subjects. The first ovulation occurred after a mean of 3.4 and 6.5 doses, and a mean of 17 and 26 days after start of treatment, in the Q7D and Q5D treatment arms, respectively.

Whenulipristal acetate was given during the follicular phase before the onset of the LH surge, ovulation occurred between 6 and 9 days of the last treatment intake in the majority of women.

These results show that UPA 30 mg single dose, when administered during the follicular phase, delays ovulation consistently by about 5 to 7 days.

Despite lengthened follicular phase and delay of LH surge the oocyte remains fertilizable as normal pregnancies have occurred after exposure to ulipristal 30 mg during the emergency contraception trials and all the parameters of the luteal phase (duration, progesterone levels) remain within the normal range.

EXAMPLE 2

The results from the clinical trial described in Example 2 were confirmed by a second clinical trial designed to evaluate the effect of a single oral dosage of 30 mg ulipristal acetate on the outcome of the leading ovarian follicle before LH surge, when the follicle was 14-16 mm in diameter.

31 women satisfying all the exclusion/inclusion criteria were enrolled. After the inclusion visit, the women entered the study and underwent ultrasound monitoring starting from Day 5 of their menstrual cycle until the lead follicle reached a diameter of 14-16 mm. At this time, the women received one single dosage of 30 mg ulipristal acetate orally. The women were then monitored daily by ultrasound and hormonal assays until the end of the 21 days treatment period or until ovulation occurred or until the mucus score reached 4 or less at 2 consecutive visits, whichever came first. After which point they were seen twice a week until the end of the study.

As shown in the table hereunder, most of the enrolled women ovulated during the on-going menstrual cycle.

TABLE 1

Outcome of the leading follicle after administration of ulipristal acetate

|  | Number of women |
|---|---|
| Ovulation | 27 |
| LUF | 2 |
| Persistent Follicle | 1 |
| Luteal phase insufficiency | 1 |
| Atresia | 0 |
| TOTAL | 31 |

As shown in FIG. 1, the ovulation occurred from 4 to 9 days after the administration of ulipristal acetate. The mean duration for the ovulation to occur was 7 days and the median duration 6 days. Similar results were obtained when ulipristal acetate was administered in women with dominant follicle having a diameter of 18 mm.

The invention claimed is:

1. A method for achieving pregnancy in a woman, the method comprising:
   (i) administering ulipristal acetate or a metabolite thereof to the woman between the 3rd day and the 12th day of her menstrual cycle, and
   (ii) scheduling an intercourse or an insemination about 4 to 9 days after the administration of ulipristal acetate or a metabolite thereof, wherein the metabolite is selected from the group consisting of CDB-3877, CDB-3963, CDB-3236 and CDB-4183.

2. The method of claim 1, wherein ulipristal acetate or the metabolite thereof is administered to the woman before the luteinizing hormone (LH) surge.

3. The method of claim 1, wherein ulipristal acetate or the metabolite thereof is administered to the woman once or twice.

4. The method of claim 1, wherein ulipristal acetate or the metabolite thereof is administered to the woman between the $4^{th}$ day and the $8^{th}$ day of her menstrual cycle.

5. The method of claim 1, wherein ulipristal acetate or the metabolite thereof induces ovulation 4 to 9 days after administration.

6. The method of claim 1 wherein the woman is a healthy woman who experiences at least one of the following features:
   variable days of ovulation,
   menstrual cycles with variable lengths, and
   menstrual cycles with a mean length up to 40 days.

7. The method of claim 1, wherein the woman suffers from ovulation dysregulation or irregular menstrual cycle, or is a perimenopausal woman.

8. The method of claim 1, wherein ulipristal acetate or the metabolite thereof is administered at a dosage ranging from 5 mg to 60 mg.

9. The method of claim 1, wherein ulipristal acetate or the metabolite thereof is administered at a dosage ranging from 20 mg to 40 mg.

10. The method of claim 1, wherein ulipristal acetate or the metabolite thereof is administered by the oral route.

11. The method of claim 1, wherein ulipristal acetate is administered to the woman.

12. A method for scheduling ovulation in a woman, the method comprising: administering ulipristal acetate or a metabolite thereof to the woman between the $3^{rd}$ day and the 12th day of her menstrual cycle, wherein the metabolite is selected from the group consisting of CDB-3877, CDB-3963, CDB-3236 and CDB-4183.

13. A method for obtaining production of a fertilizable oocyte before fertilization by an artificially reproductive technique, the method comprising: administering ulipristal acetate or a metabolite thereof to a woman between the 3rd day and the 12th day of her menstrual cycle, and optionally collecting the fertilizable oocyte about 4 to 9 days after administration, wherein the metabolite is selected from the group consisting of CDB-3877, CDB-3963, CDB-3236 and CDB-4183.

14. A method for scheduling a sexual intercourse at a day when a woman is likely to be fertile, the method comprising: administering ulipristal acetate or a metabolite thereof to the woman between the $3^{rd}$ day and the 12th day of her menstrual cycle, wherein the metabolite is selected from the group consisting of CDB-3877, CDB-3963, CDB-3236 and CDB-4183.

* * * * *